US006673418B1

(12) United States Patent
DeOlivera et al.

(10) Patent No.: US 6,673,418 B1
(45) Date of Patent: Jan. 6, 2004

(54) ABSORBENT PRODUCT HAVING A NON-WOVEN FABRIC COVER WITH A THREE-DIMENSIONAL PROFILE REGION

(75) Inventors: Ricardo DeOlivera, Lawrenceville, NJ (US); John T. Ulman, Woodbridge, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/218,972

(22) Filed: Dec. 23, 1998

(51) Int. Cl.[7] .................... B32B 5/14; B32B 27/14; B32B 3/00; B32B 7/02
(52) U.S. Cl. ................ 428/171; 428/141; 428/156; 428/170; 428/172; 428/195; 428/196; 428/198; 428/218; 442/118; 442/344; 604/370; 604/380
(58) Field of Search ................ 442/344, 118, 442/394; 428/141, 156, 170, 171, 195, 198, 218, 172, 196; 604/370, 380

(56) References Cited

U.S. PATENT DOCUMENTS

| 4,781,962 | A | | 11/1988 | Zamarripa et al. |
| 5,116,662 | A | * | 5/1992 | Morman ........................ 428/198 |
| 5,290,269 | A | * | 3/1994 | Heiman ........................ 604/378 |
| 5,417,785 | A | * | 5/1995 | Baigas, Jr. ................... 156/62.2 |
| 5,441,691 | A | * | 8/1995 | Dobrin et al. ................ 264/504 |
| 5,487,932 | A | * | 1/1996 | Dunshee ........................ 428/68 |
| 5,514,470 | A | * | 5/1996 | Haffner et al. ............... 428/246 |
| 5,531,727 | A | * | 7/1996 | Cohen et al. ................ 604/378 |
| 5,531,732 | A | | 7/1996 | Wood |
| 5,540,872 | A | * | 7/1996 | Ulman ........................ 204/119 |
| 5,795,344 | A | * | 8/1998 | Chappell ..................... 604/379 |
| 5,990,377 | A | * | 11/1999 | Chen et al. ................. 604/381 |
| 6,001,460 | A | * | 12/1999 | Morman et al. ............. 428/195 |

FOREIGN PATENT DOCUMENTS

| EP | 0 358 031 A2 | 3/1990 |
| EP | 0 829 245 A2 | 3/1998 |
| GB | 2 278 371 A | 11/1994 |
| WO | WO 97/49853 | 12/1997 |
| WO | WO 98/16177 | 4/1998 |

* cited by examiner

Primary Examiner—Cheryl A. Juska
Assistant Examiner—Christopher C. Pratt
(74) Attorney, Agent, or Firm—James P. Barr (57) ABSTRACT

An absorbent article having a body-facing cover layer, a garment facing barrier layer and an absorbent element between the cover layer and the barrier layer. The cover layer is a non-woven fabric formed from an interconnected network thermoplastic polymer fiber elements. At least a portion of the non-woven fabric is three-dimensional having a plurality of raised regions, semi-raised regions and compressed regions, the raised regions having a lower fiber density relative to the semi-raised regions, the semi-raised regions having a lower fiber density relative to the compressed regions.

18 Claims, 8 Drawing Sheets

ABSORBENT PRODUCT HAVING A NON-WOVEN FABRIC COVER WITH A THREE-DIMENSIONAL PROFILE REGION

FIELD OF THE INVENTION

This invention relates to a novel absorbent article having a nonwoven fabric as a body-facing cover layer wherein at least a portion of the nonwoven fabric has a three dimensional thickness profile.

BACKGROUND OF THE INVENTION

Nonwoven fabrics are commonly used as body-facing cover layers for disposable sanitary products. Such fabrics are generally relatively soft and conformable, capable of extended contact with external and internal body surfaces without causing chafing or allergenic reactions, and also capable of transmitting body fluids to a central absorbent element while maintaining skin dryness.

Because of the desire to provide disposable sanitary absorbent articles with body facing materials which are clean and dry, these products use synthetic fibers such as polypropylene, polyethylene, polyester and the like. Conventional nonwoven fabrics are substantially planar webs, which provide good absorbency and low fluid retention. One problem with substantially planar webs is that fluid may easily run off the lateral edges of the product. One solution to this problem is to emboss channels into the product to create obstacles to fluid flow.

SUMMARY OF THE INVENTION

It is an object of this invention to provide an absorbent article that utilizes a non-woven fabric as a body-facing cover layer, wherein at least a portion of the non-woven fabric has a three-dimensional thickness profile.

In accordance with the present invention, there has been provided a novel absorbent article having a body-facing, liquid pervious cover layer formed from a nonwoven fabric, a garment facing, liquid impervious barrier layer, and an absorbent element between the cover layer and the barrier layer, wherein at least a portion of the cover layer exhibits a three dimensional thickness profile. The portion of the non-woven cover layer that exhibits a three-dimensional thickness profile has at least three distinct regions of varying thickness; a first raised region, a second semi-raised region and a third compressed region. The raised region forms a visible protrusion above and below the surface of the non-woven fabric and has a greater thickness and lower fiber density relative to the semi-raised region. The semi-raised region has a greater thickness and a lower fiber density relative to the highly densified compressed region.

DESCRIPTION OF PREFERRED EMBODIMENTS

The present invention is directed to a novel absorbent article which is useful for absorbing body fluids such as disposable diapers, sanitary napkins, panty liners, incontinence devices and the like. The absorbent articles of the present invention have a body-facing liquid permeable cover layer, a garment facing liquid impermeable barrier layer and an absorbent element between the cover layer and the barrier layer. The cover layer comprises a non-woven fabric formed from an interconnected network of thermoplastic polymer staple fibers. At least a portion of the non-woven fabric cover layer has a three-dimensional structure. As used herein, the terminology "three-dimensional" refers to a non-woven fabric which is characterized as having at least three regions of varying thickness, a first raised region, a second semi-raised region and a third compressed region.

The raised region has a thickness that is greater than the thickness of the immediately surrounding areas of the non-woven fabric and is characterized as being a protrusion which is formed by a rearrangement of fibers out of the plane of the non-woven fabric, i.e. in the 'z' direction in an 'x, y, z' coordinate system. The fiber density of the raised region is less than the fiber density of the semi-raised region and the semi-raised region has a lower fiber density relative to the compressed region.

The compressed regions of the non-woven fabric have a fiber density in a range of about 0.05 g/cc to about 0.17 g/cc, preferably from about 0.1 g/cc to 0.12 g/cc. This generally corresponds to a thickness of from about 0.005 mm to about 0.06 mm. The semi-raised regions of the non-woven fabric have a fiber density of from about 0.04 g/cc to about 0.11 g/cc, preferably from about 0.06 g/cc to about 0.09 g/cc/ This generally corresponds to a thickness from about 1.5 to 40 times the thickness of the compressed regions, preferably about 8 to 30 times the thickness of the compressed regions. The raised regions of the non-woven fabric have fiber density in a range of from 0.027 g/cc to about 0.07 g/cc, preferably from about 0.04 g/cc to about 0.06 g/cc which generally corresponds to a thickness from about 6 to 800 times the thickness of the compressed regions, preferably about 10 to 50 times the thickness of the compressed regions. The raised regions are always thicker than the semi-raised regions, generally 1 to 40 times thicker and preferably 1.5 to 2.5 times thicker than the semi-raised regions.

The raised regions, semi-raised regions and compressed regions are preferably formed in a repeating pattern across a substantial portion of the non-woven cover layer to create a 'quilted' appearance on the surface of the non-woven fabric wherein the raised regions resemble pyramidal shaped pillows. These low fiber density pillows provide a soft texture to the non-woven fabric in the region of the three-dimensional profile. In addition, the three-dimensional profile possesses an irregular, undulating surface created by the raised regions and adjacent semi-raised regions and compressed regions. These surface irregularities function as barriers to fluid flow across the surface of the cover layer. In a preferred embodiment, the three-dimensional portion of the cover layer is located in a central region of the absorbent article and in a most preferred embodiment, the three-dimensional portion of the cover layer is located in opposite transverse end regions and in a center region of the absorbent article.

Suitable non-woven fabrics for use in the present invention are formed from an interconnected network thermoplastic polymer fibers, preferably staple fibers. In a preferred embodiment, the non-woven fabric is formed from a homogeneous blend of high denier staple fibers and low denier staple fibers. These staple fibers will generally have a denier in a range of from 1.5 denier to 15 denier and preferably have a denier in the range of from 3 denier to 6 denier. The high denier staple fibers and the low denier staple fibers preferably differ by at least one denier, and preferably differ by 2 denier. In a preferred embodiment, the low denier staple fibers have a denier of from about 1.5 to 4 and preferably have a denier of about 3. The high denier staple fibers have a denier of from about 4 to 15 and preferably have a denier of about 5. The high denier staple fibers are present in the non-woven fabric in an amount of from 10 to 90 weight percent, preferably in a range of from 30 to 70 weight percent, and most preferably in a range of from 40 to 60 weight percent. The low denier staple fibers are present in the non-woven fabric in an amount of from 90 to 10 weight percent, preferably in a range of from 30 to 70 weight percent, and most preferably in a range of from 40 to 60 weight percent based on the total weight of the non-woven fabric.

In accordance with this embodiment of the present invention the fibrous web may be formed by homogeneously mixing a combination of low denier and high denier fibers. The low denier staple fibers and high denier staple fibers may be conveniently homogeneously mixed in an air mixing chamber and then either carded to form a carded web or randomly laid on a foraminous forming structure to form a fibrous web.

Suitable fibers for use in the present invention include, but are not limited to, synthetic polymeric fibers formed from thermoplastic resins such as polypropylene, polyester, polyethylene, polyacrylate, and the like and combinations thereof A preferred synthetic polymeric fiber is polypropylene. As noted above, the fibers used to form the non-woven fabric of the present invention are staple fibers, and generally have a fiber length in a range of from 1 inch to 4 inches, and preferably have a fiber length in the range of from 1.25 inches to 3 inches.

The non-woven fabrics of the present invention may be formed by conventional non-woven fabric forming processes which are well known in the art, is including, but not limited to, dry laid web forming processes, carded web forming processes, air laid web forming processes, spun-bonded web forming processes, and the like. In all of these manufacturing processes it is important that a majority of the fibers be oriented in substantially the same direction (often referred to a the 'machine' direction). Typically, any process that utilizes a moving foraminous surface will provide a fiber-oriented web. A preferred method for producing suitable non-woven webs is a carded web forming process. The resultant non-woven fabrics will have a greater tensile strength in the continuous machine direction of the web relative to the tensile strength in a cross direction (which is substantially perpendicular to the machine direction).

The fibrous web may be stabilized into a nonwoven fabric by conventional processes such as by thermobonding, resin bonding, spunlacing or the like. It is preferred that a thermobonding process be used to stabilize the fibrous web. In a conventional thermobonding process, the web of fibers is fed into a calendering station equipped with a heated anvil roll and a patterned embossing roll which simultaneously compresses and thermally bonds the fibers to stabilize the web into a non-woven fabric. An alternative thermobonding process involves forcing heated air through the web and is generally known as a through-air bonding process. In a resin bonding process, a fibrous web is formed as above and passed through a forming drum equipped with a series of water spray nozzles (i.e. having a pressure of about 200 psi) which are capable of lightly entangling the fibers. The entangled web is then de-watered and fed into a binder printing station where the fabric is impregnated with a binder. The binder-impregnated fabric is then dried and cured in an oven. Alternatively, the fibrous web may be sprayed with resin powders under vacuum and then through-air bonded in an oven. Finally, in a spunlace process, the homogeneous blend of low and high denier staple fibers is passed through a series of high pressure water jets, i.e. having a pressure of from 500 to 1500 psi. to highly entangle the fiber web into a stabilized fabric. The fabric is then de-watered and dried. All of the foregoing processes are well known to those of ordinary skill in the art and the choice of one process over another process is not, per se, critical to the invention, provided of course that the resultant non-woven fabric has sufficient structural integrity to permit it to be adapted as a cover material for absorbent articles. In general, a non-woven fabric has sufficient structural integrity when the tensile strength is about one pound per inch. Sufficient structural integrity is achieved when the bonding area comprises from 10 to 40 percent of the total nonwoven fabric area, and is preferably in a range of from 15 to 30 percent of the total fabric area, and most preferably from 20 to 26 percent of the total fabric area. It is preferred that the non-woven fabrics of the present invention be a carded web formed by a thermobonding process utilizing hot patterned calender rolls.

The ability of a non-woven fabric to mask absorbed fluids, particularly menstrual fluid, is an important consideration in the development of body-facing covers for absorbent articles. Accordingly, the fibers of the present invention are preferably provided with a colorant. A preferred color is a white color, preferably formed by incorporating titanium dioxide into the fibers used to form the non-woven fabric. The titanium dioxide content of the fibers is present in an amount to provide sufficient opacity to the fiber and thereby provide good masking of absorbed fluids. The titanium dioxide content is preferably between about 1 to 6 weight percent, and is most preferably in a range of from 2 to 2.5 weight percent. An alternative colorant is calcium carbonate, and may be present in the fibers in a range of from 50 to 20 weight percent. Mixtures of calcium carbonate and titanium dioxide may also be used.

It is generally desirable that the body-facing cover layer have a durable hydrophilic finish so that the portion of the absorbent article in contact with a wearer's skin remains hydrophilic after multiple fluid introductions. Hydrophilic finishes provide enhanced body fluid transport away from the wearer which aids in transporting the body fluids to the underlying absorbent element. The fibers of the present invention may be treated with a durable hydrophilic surface active agent, such as, for example, a nonionic surfactant which is commercially available under the tradename ATMER™ from ICI Polymer Additives, New Castle, Del. Other suitable hydrophilic surface active agents include, but are not limited to sodium salts of dioctyl sulfosuccinate (commercially available under the designation AEROSOL OT™), non-ionic polyoxyethylene sorbitan monolaurate (commercially available under the designation TWEEN 20™), or the like. The durable hydrophilic finish may be applied to the fiber surface by dipping fibers into an aqueous solution of the desired surface active agent or by spraying an aqueous solution of the desired surface active agent onto outer surface and subsequently drying the fibers. The surface active agent may be deposited on the non-woven fabric by means of a roller which has been wetted with an aqueous solution of the surface active agent which is passed over inner surface of non-woven fabric so as to deposit the surface active agent near and on an inner surface while the outer surface retains a substantially hydrophobic character. Alternatively, internal hydrophilic surfactants or wetting agents can be incorporated directly into the thermoplastic polymer during manufacture of the fibers. Suitable wetting agents for include non-ionic surfactants based on ethylene oxide-fatty alcohol ethers, ethoxylated adducts of propylene oxide with propylene glycol, fatty esters or sorbitol and glycerol, and the like.

The non-woven fabrics of the present invention generally have a basis weight in a range of from 20 grams per square meter (gsm) to 50 gsm, preferably in a range of from 30 gsm to 35 gsm and have a bulk (thickness) of between about 10 to 40 mils, preferably from about 15 to 35 mils, and most preferably from 20 to 30 mils.

The non-woven fabric may have a bonding pattern made up of continuous bond lines or may be a series of discontinuous bond areas and is preferably an intermittent series of discrete dots. It is important the bonding pattern be in a line-like order or array. That is, the pattern of bond areas should be arranged in a plurality of regular arrays in either a curved or linear line-like order wherein at least a portion of the bonds within a particular line-like array are closer to adjacent bonds within the line-like array than they are to bonds in adjacent line-like arrays. The regular array of depressed bonds define therebetween non-bonded regions. The line-like pattern of bond areas are preferably uniformly arranged across the non-woven fabric to provide regions of high density bond areas in a line like order and adjacent areas of non-bonded semi-raised regions between the regions of high density bond areas. While the bond areas are preferably uniformly arranged across the non-woven fabric, the average bond density is generally not uniform across the surface of the nonwoven fabric and may vary widely depending upon the particular pattern of bond areas. It is considered an important feature of the present invention that the pattern of line-like arrays of bonds be oriented in a direction that is neither parallel to nor perpendicular to the fiber orientation of the thermoplastic fibers in the non-woven fabric. As previously discussed, suitable non-woven fabrics for use in this invention are formed from a fiber-oriented web. In accordance with this feature of the present invention, the pattern of bonds should not be oriented in a parallel or perpendicular direction to the direction of the fiber orientation, particularly in the region where a three-dimensional profile is desired.

When the non-woven fabric of the present invention is subjected to a tensioning force applied in a direction which is substantially perpendicular to the direction of the fiber orientation of the non-woven fabric, at least a portion of the semi-raised regions will expand three-dimensionally above and below the plane of the non-woven fabric to form raised regions having a lower fiber density relative to the semi-raised regions and to the compressed bond areas. More specifically, when subjected to a tensioning force, the semi-raised regions expand vertically out of the plane of the fabric to form a plurality of raised regions having a greater thickness than the adjacent regions. This results in a non-woven fabric having regions which, if not subjected to a tensioning force, will include only high density bond areas surrounded by adjacent less dense, semi-raised areas of low bond density, and other regions which when subjected to a tensioning force, form a region having a three-dimensional profile having three distinct areas of varying thickness and fiber density. The three distinct areas include the relatively dense bond areas, the less dense semi-raised regions and low density raised regions having the lowest fiber density. Thus, the three-dimensional fabric possesses three distinct regions, each region having a thickness and fiber density that is different than an adjacent region. The regions of line-like bond areas form a plurality of compressed high fiber density, low fabric thickness regions. The non-bonded regions form a plurality of semi-raised regions or raised regions depending of course on whether that portion of the non-woven fabric is subjected to a tensioning force, wherein the raised regions have a lower fiber density relative to the semi-raised regions and the semi-raised compressed regions.

The spacing between each line-like array of bonds may vary widely depending upon the nature of the specific bonding pattern chosen. For spacing between each bond in a contiguous line-like order bond pattern, the spacing may be as small as 0.5 mm and can be as large as a few centimeters. For spacing between adjacent line like orders, the spacing is generally about 2 mm to 15 mm, and is preferably about 7 mm to 10 mm.

The bond densities can vary widely depending of course on the desired overall strength of the nonwoven fabric. When the bonds are in the form of dots, the bond densities generally range from about 1 bond per $cm^2$ to about 1300 bonds per $cm^2$, preferably 3 bonds per $cm^2$ to 300 bonds per $cm^2$ and most preferably 10 bonds per $cm^2$ to 200 bonds per $cm^2$. The size of the diameter of individual bonds for dot bonds can range from about 0.1 mm to about 5 mm. The spacing between dot bonds within the line-like order can range from about 0.05 mm to about 5 mm, preferably from about 0.2 mm to about 0.3 mm. Individual dot areas can range from about 0.1 $mm^2$ to about 80 $mm^2$, preferably from about 0.5 $mm^2$ to about 15 $mm^2$ and most preferably about 5 $mm^2$. The dot density can range from about 1 dot/$cm^2$ to about 1500 dots/$cm^2$, preferably from about 3 dots/$cm^2$ to about 300 dots/$cm^2$, and most preferably between about 10 dots/$cm^2$ to 200 dots/$cm^2$. For bond lines, the bond width is about 1 mm to 5 mm and the bond length is about 10 mm to about 300 mm. Combinations of dots and lines is also contemplated.

The tension applied to the non-woven fabric may be applied by stretching the nonwoven fabric either prior to, during or after its incorporation onto the absorbent article. Tension may be imparted by any conventional tensioning means. Examples of tensioning means include, but are not limited to the use of angled rollers which impart a laterally outward tension to the longitudinal side edges of a continuous web of nonwoven fabric as it moves along a conveyor system, by maintaining the longitudinal side edges of a nonwoven web in a fixed width while forcing the fabric to conform to a three-dimensional structure, or by imparting one or more embossed channels into the upper surface of as absorbent article to create one or more depressions into the upper surface of the absorbent article, thereby tensioning the non-woven fabric cover layer and creating the three-dimensional profile. The amount of tension applied to the non-woven fabric can vary widely depending of course on the tensile strength of the non-woven fabric and is not, per se, critical to the invention, provided of course that the amount of tension sufficient to impart the desired level of three-dimensionally without damaging the fabric. In general, a sufficient tension is applied when the nonwoven fabric is stretched beyond its normal, non-stretched width by about 5%, preferably 10% and most preferably from 15 to 20%

Figure 1:
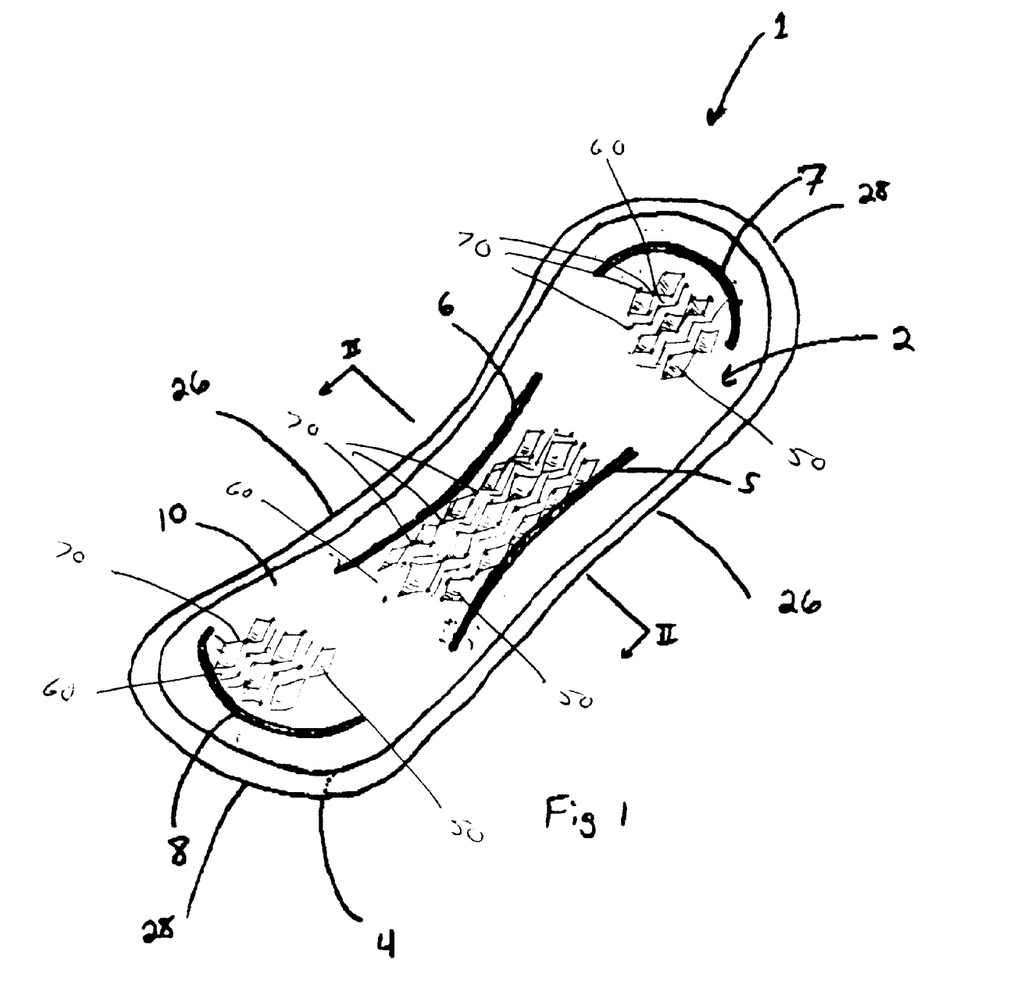
FIG. 1 is a plan view of a preferred embodiment of the absorbent article of the present invention for use by a woman for feminine hygiene.
Figure 2:
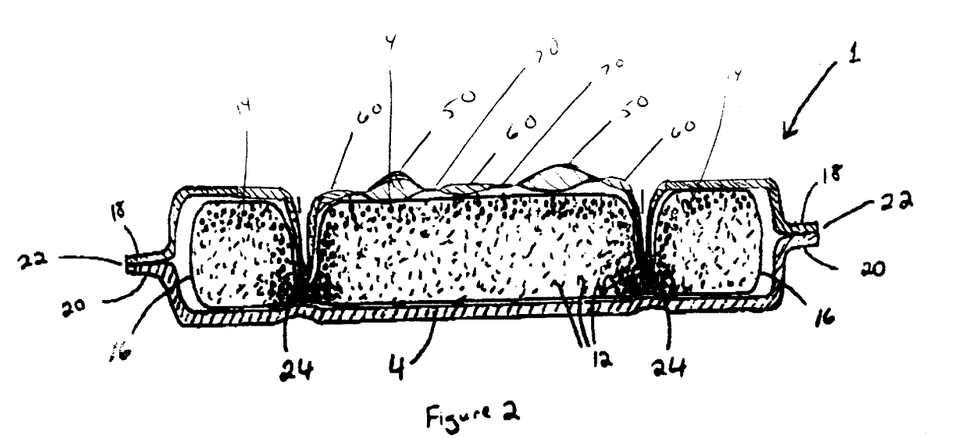
FIG. 2 is a cross-sectional view taken along line II—II of FIG. 1.
Figure 3:
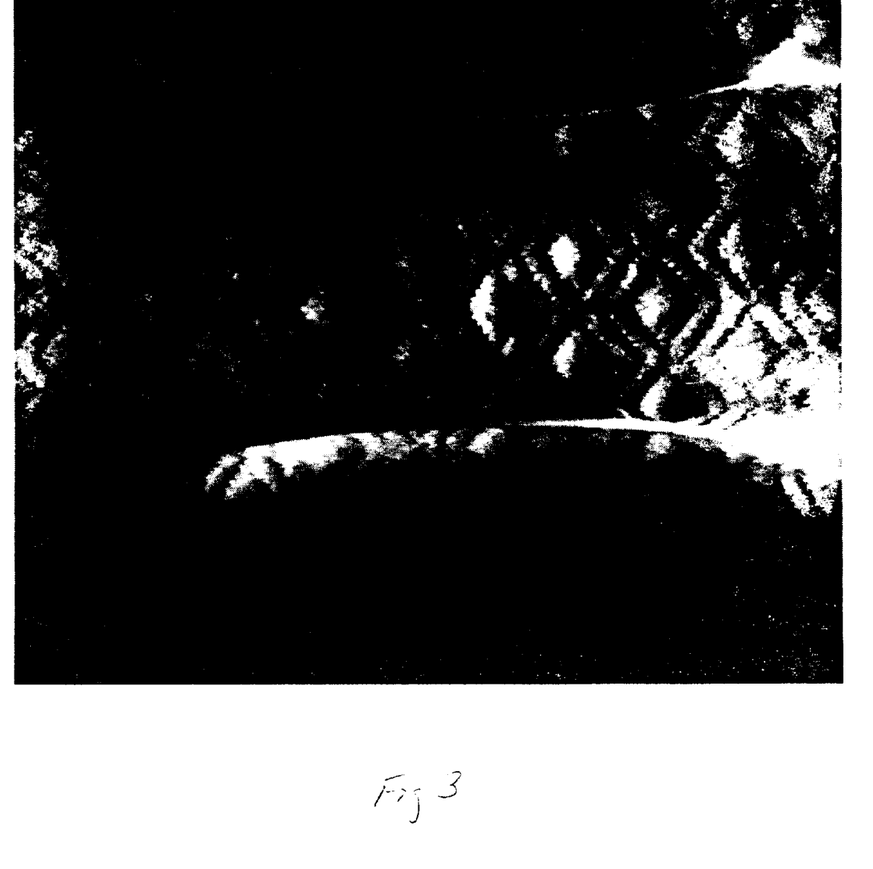
FIG. 3 is a photograph of central region of a sanitary napkin having a three dimensional profile.
Figure 4:
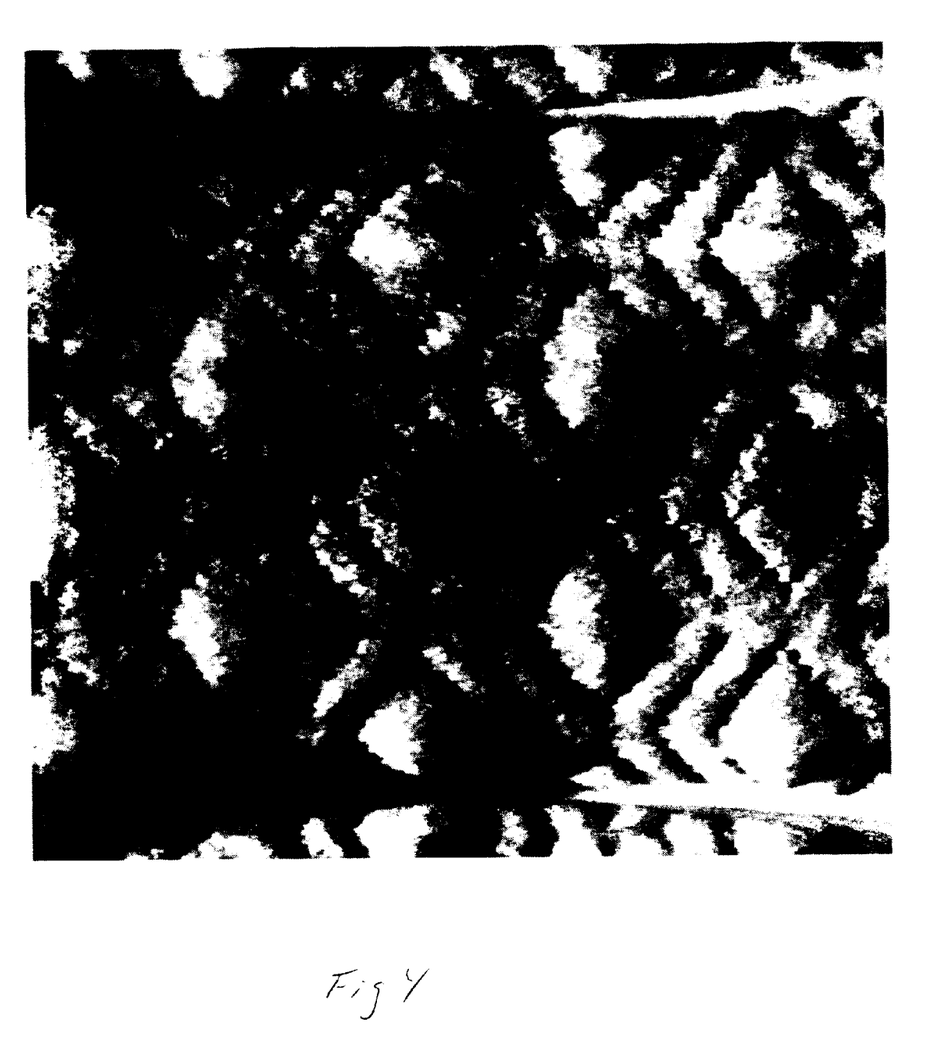
FIG. 4 is the photograph of the sanitary napkin shown in FIG. 3 which was magnified two times.
Figure 5:
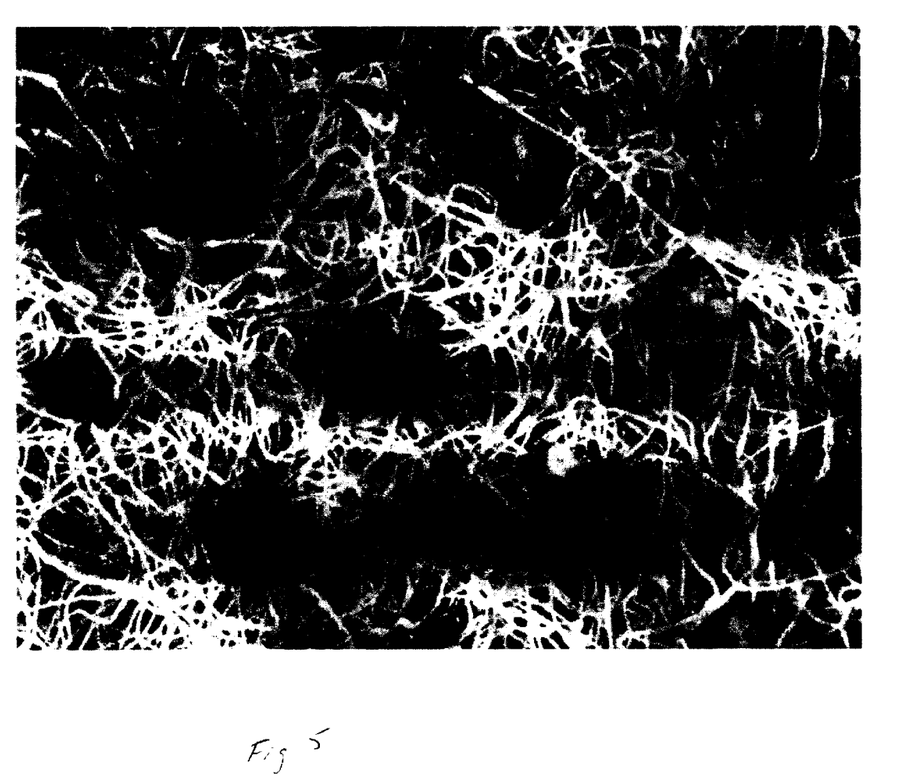
FIG. 5 is a photomicrograph of a top view of a conventional non-woven fabric having a bond pattern which is not in a line-like array.
Figure 6:
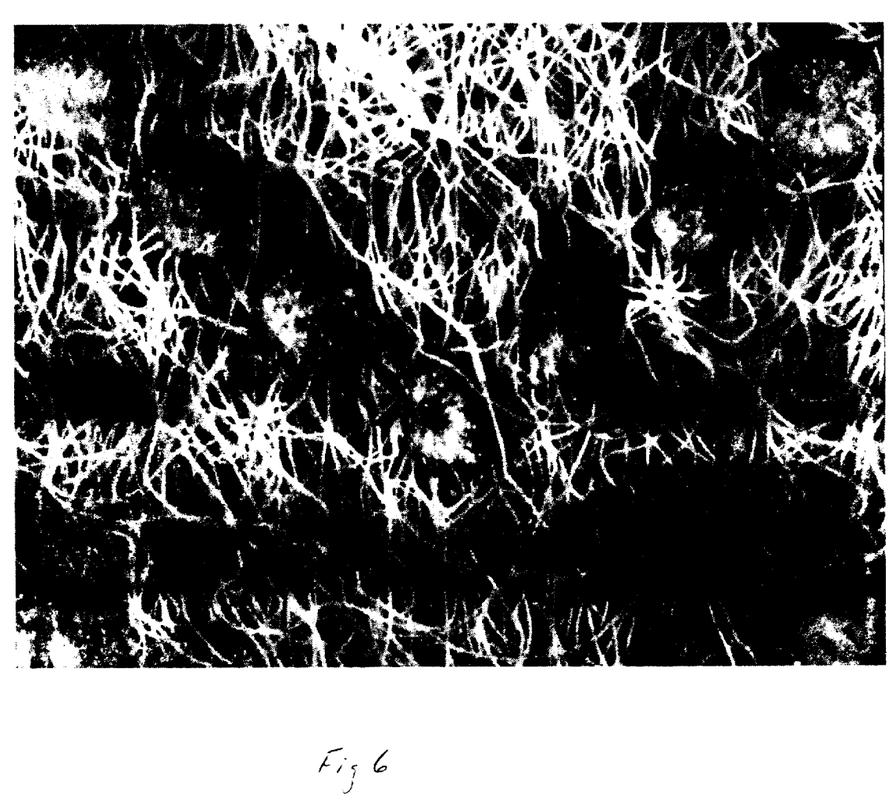
FIG. 6 is a photomicrograph of a top view of a non-woven fabric of the present invention having a bonding pattern in a line-like array.

Referring to FIG. 1, there is shown an absorbent article for use by a woman for feminine hygiene according to this invention. The article 1 is comprised of a generally rectangular absorbent element 2 overlying a continuous barrier film layer 4. The article has densified stabilizing regions that take the form of densified embossed channels 5, 6, 7, 8 adjacent to and inward from the longitudinal sides and ends of the article. A liquid permeable body-facing cover layer 10 covers the absorbent element 2 and forms the top surface of the article. The cover layer 10 has three distinct regions which exhibit a three-dimensional profile, one region in adjacent a first transverse end, a second region adjacent an opposite transverse end and a third region centrally located in the article. The three-dimensional profile includes a raised region 50, a semi-raised region 60 and a compressed region 70. As is shown in FIG. 2, the raised region 50 has a greater thickness than the semi-raised region 60 which has a greater thickness than the compressed region 70. The regions having a three-dimensional profile are located between the embossed channels, 5, 6, 7, 8, which impart a tensioning force to the non-woven cover layer 10. The absorbent element 2 may optionally comprise a combination of cellulosic fibers 12 and superabsorbent polymer particles 14.

The embossed channels 5, 6, 7, 8 may have any shape or configuration and may comprise continuous segments, discontinuous segments, straight segments, curved segments or combination thereof It is preferred that the each respective embossed channel be a curved, continuous segment. If the embossed channels are formed by discontinuous segments, it is preferred that the segments not be spaced apart from each other by more than 0.25 inches in order to maintain good fluid barrier properties and impart a controlled deformation and resistance to bunching for the absorbent article. It is preferred that embossed channels in the transverse end regions have at least one perpendicular component that is generally orthogonal to the lateral component and generally parallel to the central longitudinal axis of the absorbent product, and with the perpendicular component being closer to the longitudinal edge than it is to the central longitudinal axis. The perpendicular component need not be strictly orthogonal to the lateral component. It may also be at some acute or obtuse angle to the lateral component, and may extend towards the transverse edge, towards the central region, or both. It is important that the embossed channel be located inwardly of the edges of the transverse end region of the absorbent article, and is preferably approximately between 0.125 inches and 2.5 inches inwardly of the edges of each respective transverse end region. It is preferred that the embossed channels 5, 6, 7, 8 be compressed in an amount sufficient to provide a density, measured at the bottom 24 most dense portion of the channel, of at least about 0.5 g/cc, more preferably, the density is between about 0.5 g/cc and 1.3 g/cc.

As shown in the Figures, the absorbent element 2 is contained between the article's facing or cover layer 10 and the barrier layer 4. The nonwoven cover layer 10 and barrier layer 4 preferably extend beyond the edges 16 of the absorbent element to form peripheral cover extensions 18 and barrier extensions 20. These peripheral cover extensions 18 and barrier extensions 20 are joined to one another to form a flange seal 22 around the outside edges of the article. The flange seal may be formed by any sealing means known in the art, including without limitation, heat sealing, ultrasonic sealing, adhesive sealing, or mechanical sealing. Although the preferred article of this invention is made with a flange seal, such a method of sealing the edges of the article is not necessary to the invention. The edges of the article may also be sealed by means of wrapping the cover layer, the barrier layer, or both layers around the edges.

The body-facing cover layer 10 and garment-facing fluid impermeable barrier layer 4 are usually substantially coextensive and are joined together about the periphery of the absorbent element 2 by thermal fusion, adhesive, or in any other convenient manner to thereby define the outer edges of the absorbent article. If desired, the absorbent element 2 may be anchored to garment-facing fluid impermeable barrier sheet by one or more glue lines.

The fluid impermeable garment facing barrier layer may be any flexible material that prevents the transfer through it of fluid but does not necessarily prevent the passages of gases. Commonly used materials are polyethylene or polypropylene films. Other suitable polymeric film materials that may be used as impermeable barriers include, but are not limited to polyesters, polyamides, polyethylene vinyl acetate, polyvinyl chloride, and polyvinylidene chloride, and the like and combinations thereof Co-extruded and laminated combinations of the foregoing, wherein such combinations are permitted by the chemical and physical properties of the film, may be used. Fluid impermeable foams and repellent treated papers may also be used. Films that are fluid barriers, but permit gases to transpire, i.e., "breathable films", may be used. These may be chosen from polyurethane films and from micro-porous films, where microporosity is created by ionizing radiation or by leaching out of soluble inclusions using aqueous or nonaqueous solvents. Fabrics whose surfaces have been made repellent or whose pores are small by virtue of close packing of fibers, or whose pores have been reduced in size by closing off large liquid admitting pores, may also be used alone, or together with breathable films, as breathable barriers. A suitable backing sheet material can be an opaque polyolefin, e.g., polyethylene, web impermeable to body fluids and about 0.001 inch thick. Another suitable sheet material for this purpose is a polyester, e.g., polyethylene terephthalate, web having a thickness of about 0.0005 inch.

The absorbent element can be a fluffy batt cut from a relatively loose web of non-woven fibers having a relatively high absorptive capacity. The absorbent element is usually of a rectangular configuration, and may optionally be shaped and contoured to have inwardly curved side edges such as an hourglass shape. The absorbent element is somewhat smaller than the backing sheet and non-woven bodyside liner. The absorbent element may also be a fibrous batt formed from cellulosic pulp fibers.

The absorbent article may optionally comprise a multi-layered absorbent structure which may contain, in addition to the absorbent element, a transfer layer, which is a low density fluid accepting and fluid releasing layer, usually located between the absorbent element and the permeable body-facing cover layer. The transfer layer may be comprised of relatively less hydrophilic materials and structures, than is contained in the absorbent element, such as of webs of meltblown polypropylene or polyester fibers. Such webs may also contain wood pulp entrained within. Transfer layers may also be comprised of low density, highloft nonwoven webs comprised of wood pulp and synthetic fibers such as polyethylene, polyester, polypropylene, polyamide and polyacrylonitrile. Such highloft webs may be bonded with chemical binders or by thermal means such as by through-air bonding.

The thickness of the absorbent structure will generally range from a few millimeters thick for 'ultra-thin' type of products to about 10 to 15 millimeters thick for more conventional 'thick' products. The thickness of the products may be substantially uniform throughout the length and width of the absorbent element or may have a tapered profile wherein a central region of the absorbent element is thicker than the transverse end and/or side regions of the absorbent element. For example, a particularly preferred thickness profile is an absorbent structure that is two to three times thicker in the central region than it is in the end regions.

The garment-facing fluid impermeable barrier sheet may be adhered to the body-facing cover layer in a flange seal extending from the sides of the absorbent element. When the body-facing cover layer and garment facing barrier layer are adhered to each other in a flange seal, the body facing layer may additionally be wrapped around the flange seal about the body facing layer; or the garment facing layer may additionally be wrapped around the flange seal about the body facing layer.

EXAMPLE

The nonwoven fabric of the present invention was evaluated in a region having a three-dimensional thickness profile for its fluid penetration rate, repeated strike through rates and air permeability relative to a conventional non-woven fabric having the same basis weight and fiber denier. The results of this evaluation are provided in the following Tables 1–3. Table 1 provides the Air Permeability data (measured in cubic feet of air per minute per square yard of fabric) for the conventional non-woven fabric and the three-dimensional fabric of the present invention when tensioned in an amount sufficient to stretch the nonwoven fabric in a cross direction (CD) 10% and 20% (110% and 120% of the original fabric width).

TABLE 1

AIR PERMEABILITY DATA FOR COVERSTOCK
Units: cfm/sq ft

| | STD COVER | | | 3-D COVER | | |
|---|---|---|---|---|---|---|
| Sample # | CONTROL | 10% CD Elong. | 20% CD Elong. | CONTROL | 10% CD Elong. | 20% CD Elong. |
| 1 | 424 | 572 | 610 | 640 | 716 | 758 |
| 2 | 437 | 590 | 612 | 640 | 726 | 764 |
| 3 | 443 | 609 | 612 | 640 | 728 | 770 |
| 4 | 446 | 619 | 647 | 647 | 730 | 770 |
| 5 | 448 | 619 | 661 | 649 | 730 | 776 |
| 6 | 454 | 620 | 663 | 653 | 743 | 781 |
| 7 | 454 | 620 | 675 | 655 | 745 | 787 |
| 8 | 464 | 634 | 692 | 658 | 748 | 793 |
| 9 | 472 | 639 | 694 | 660 | 752 | 793 |
| 10 | 474 | 639 | 694 | 660 | 752 | 793 |
| 11 | 474 | 645 | 696 | 661 | 756 | 798 |
| 12 | 478 | 652 | 696 | 672 | 761 | 809 |
| 13 | 482 | 667 | 712 | 675 | 762 | 809 |
| 14 | 492 | 667 | 715 | 675 | 762 | 815 |
| 15 | 513 | 669 | 716 | 682 | 768 | 821 |
| 16 | 515 | 670 | 730 | 697 | 770 | 831 |
| 17 | 522 | 673 | 762 | 711 | 781 | 842 |
| 18 | 535 | 682 | 762 | 712 | 811 | 847 |
| 19 | 540 | 687 | 780 | 723 | 823 | 847 |
| 20 | 542 | 696 | 781 | 723 | 797 | 884 |
| AVG, | 480 | 643 | 695 | 672 | 758 | 804 |
| STDEV | 36 | 33 | 52 | 28 | 28 | 33 |

As is evident from the data, the non-woven fabric of the present invention (3-D Cover) provided enhanced air permeability relative to a conventional non-woven fabric (STD Cover).

A sanitary napkin having a conventional non-woven fabric cover was compared to a sanitary napkin having the nonwoven fabric of the present invention for its ability to allow fluid to penetrate through to the subjacent absorbent element. The results are illustrated below in Tables 2 for the conventional nonwoven fabric cover and Table 3 for the nonwoven fabric of the present invention.

TABLE 2

| | FLUID PENETRATION TEST | | REPEATED STRIKETHROUGH | | | | | |
|---|---|---|---|---|---|---|---|---|
| | Sec | | 1 × 2 cc | 2 × 2 cc | 3 × 2 cc | 4 × 2 cc | 5 × 2 cc | 6 × 2 cc |
| 1 | 13.97 | 1 | 5.48 | 7.50 | 7.55 | 8.12 | 9.31 | 8.64 |
| 2 | 12.99 | 2 | 5.59 | 7.54 | 8.30 | 8.48 | 9.04 | 9.29 |
| 3 | 13.66 | 3 | 4.81 | 8.00 | 7.95 | 8.42 | 8.66 | 8.82 |
| 4 | 13.70 | 4 | 5.54 | 8.43 | 9.01 | 9.74 | 10.04 | 9.80 |
| 5 | 14.06 | 5 | 5.43 | 7.96 | 7.83 | 8.27 | 8.58 | 7.86 |
| 6 | 12.22 | 6 | 4.98 | 6.96 | 7.31 | 7.85 | 7.76 | 8.09 |
| 7 | 12.20 | 7 | 5.58 | 6.81 | 7.07 | 7.40 | 7.94 | 8.62 |
| 8 | 13.86 | 8 | 5.32 | 7.52 | 7.51 | 7.74 | 8.52 | 7.83 |
| 9 | 13.69 | 9 | 5.41 | 7.59 | 7.61 | 8.81 | 9.18 | 9.64 |
| 10 | 13.59 | 10 | 5.32 | 7.64 | 7.10 | 7.40 | 8.51 | 9.14 |
| 11 | 13.73 | 11 | 5.47 | 7.14 | 7.93 | 8.74 | 8.89 | 8.95 |
| 12 | 11.21 | 12 | 5.41 | 7.61 | 8.01 | 8.15 | 8.80 | 9.25 |
| 13 | 12.25 | 13 | 5.06 | 7.19 | 6.61 | 6.70 | 6.96 | 6.31 |
| 14 | 13.23 | 14 | 5.80 | 8.25 | 8.54 | 9.43 | 9.36 | 8.95 |
| 15 | 13.25 | 15 | 5.54 | 7.42 | 7.74 | 8.43 | 8.98 | 9.48 |
| 16 | 14.18 | 16 | 4.91 | 7.58 | 7.27 | 7.83 | 7.66 | 8.06 |

TABLE 2-continued

| | FLUID PENETRATION TEST | | REPEATED STRIKETHROUGH | | | | | |
|---|---|---|---|---|---|---|---|---|
| | Sec | | 1 × 2 cc | 2 × 2 cc | 3 × 2 cc | 4 × 2 cc | 5 × 2 cc | 6 × 2 cc |
| 17 | 13.71 | 17 | 5.05 | 7.17 | 7.01 | 6.47 | 6.35 | 6.93 |
| 18 | 13.76 | 18 | 5.40 | 7.96 | 8.44 | 8.97 | 9.08 | 9.94 |
| 19 | 12.95 | 19 | 5.37 | 7.40 | 7.85 | 8.12 | 8.35 | 8.78 |
| 20 | 13.20 | 20 | 5.56 | 7.86 | 7.67 | 8.61 | 8.92 | 9.35 |
| AVG | 13.2705 | AVG | 5.3515 | 7.5765 | 7.7155 | 8.184 | 8.5445 | 8.6865 |
| STD | 0.770 | STD | 0.259 | 0.415 | 0.581 | 0.811 | 0.861 | 0.939 |
| MIN | 11.21 | MIN | 4.81 | 6.81 | 6.61 | 6.47 | 6.35 | 6.31 |
| MAX | 14.18 | MAX | 5.80 | 8.43 | 9.01 | 9.74 | 10.04 | 9.94 |

TABLE 3

| | FLUID PENETRATION TEST | | REPEATED STRIKETHROUGH | | | | | |
|---|---|---|---|---|---|---|---|---|
| | Sec | | 1 × 2 cc | 2 × 2 cc | 3 × 2 cc | 4 × 2 cc | 5 × 2 cc | 6 × 2 cc |
| 1 | 11.53 | 1 | 4.07 | 5.10 | 6.16 | 6.84 | 7.41 | 8.17 |
| 2 | 12.97 | 2 | 4.80 | 6.21 | 5.60 | 6.90 | 7.38 | 8.08 |
| 3 | 13.03 | 3 | 4.11 | 5.79 | 5.63 | 6.62 | 6.73 | 6.90 |
| 4 | 12.90 | 4 | 3.95 | 5.68 | 5.49 | 5.54 | 5.90 | 5.89 |
| 5 | 11.66 | 5 | 3.94 | 5.84 | 5.69 | 5.89 | 6.73 | 6.40 |
| 6 | 10.96 | 6 | 4.57 | 6.28 | 6.44 | 6.96 | 7.24 | 8.24 |
| 7 | 12.83 | 7 | 5.04 | 6.62 | 6.00 | 6.97 | 6.99 | 8.36 |
| 8 | 11.70 | 8 | 4.18 | 5.80 | 6.09 | 6.35 | 6.68 | 8.62 |
| 9 | 12.93 | 9 | 5.07 | 7.19 | 7.40 | 7.68 | 8.04 | 11.30 |
| 10 | 10.83 | 10 | 4.59 | 7.10 | 7.13 | 7.01 | 6.88 | 8.25 |
| 11 | 10.59 | 11 | 4.61 | 5.68 | 6.00 | 7.32 | 6.52 | 6.64 |
| 12 | 11.28 | 12 | 4.52 | 6.26 | 6.97 | 7.08 | 7.05 | 7.66 |
| 13 | 11.74 | 13 | 5.10 | 7.14 | 7.26 | 7.41 | 7.47 | 7.51 |
| 14 | 12.67 | 14 | 4.26 | 5.59 | 5.98 | 6.36 | 6.60 | 6.20 |
| 15 | 11.86 | 15 | 5.33 | 7.14 | 7.61 | 7.91 | 8.08 | 8.01 |
| 16 | 12.78 | 16 | 5.20 | 7.61 | 6.52 | 6.47 | 7.01 | 7.48 |
| 17 | 11.93 | 17 | 4.66 | 6.69 | 6.69 | 7.11 | 7.18 | 7.39 |
| 18 | 13.35 | 18 | 4.72 | 6.36 | 6.66 | 7.19 | 7.32 | 7.61 |
| 19 | 11.85 | 19 | 4.57 | 5.99 | 5.88 | 6.40 | 7.10 | 7.02 |
| 20 | 12.88 | 20 | 5.13 | 6.99 | 6.98 | 7.67 | 7.45 | 7.53 |
| AVG | 12.1135 | AVG | 4.621 | 6.353 | 6.409 | 6.884 | 7.088 | 7.663 |
| STD | 0.835 | STD | 0.433 | 0.680 | 0.651 | 0.599 | 0.508 | 1.146 |
| MIN | 10.59 | MIN | 3.94 | 5.10 | 5.49 | 5.54 | 5.90 | 5.89 |
| MAX | 13.35 | MAX | 5.33 | 7.61 | 7.61 | 7.91 | 8.08 | 11.3 |

Figure 7:
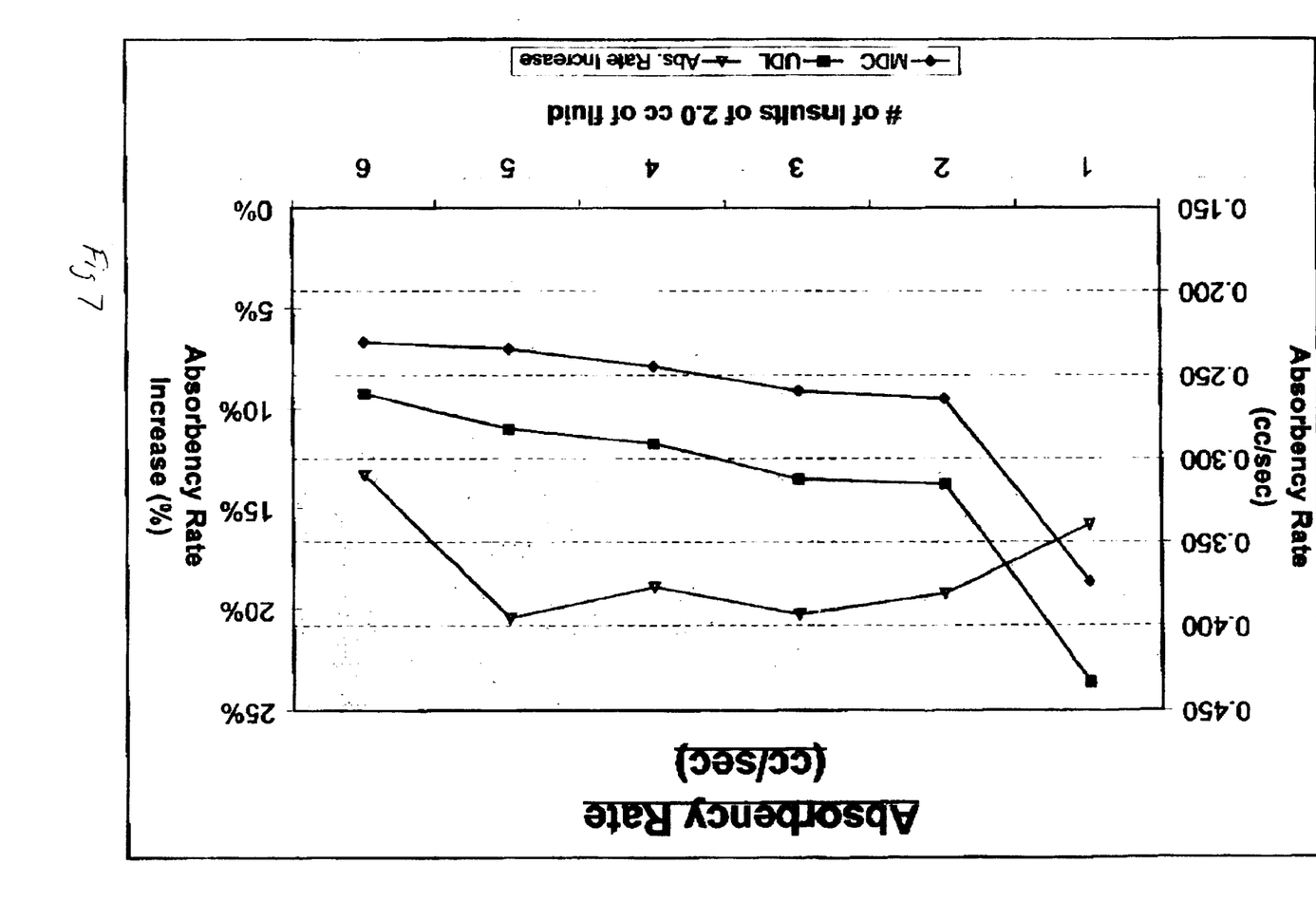
FIG. 7 is a graph comparing the absorbency rate of a conventional non-woven fabric and the non-woven fabric of the present invention.
Figure 8:
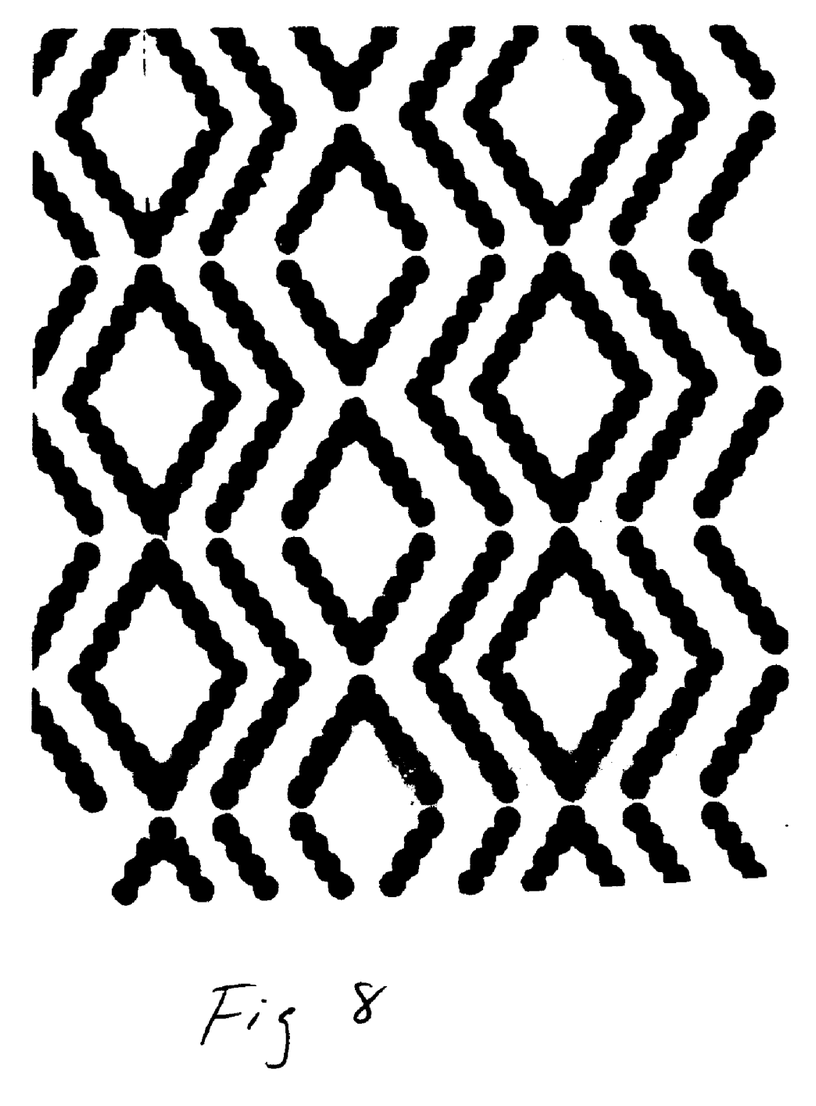
FIG. 8 is an illustration of a preferred dot bonding pattern in a line-like array

As is apparent from the above Tables, the nonwoven fabric of the present invention provided superior fluid penetration rates. The above fluid penetration rates were plotted in graphical form as illustrated in FIG. 7 wherein MDC represents the conventional nonwoven fabric cover and UDL represents the three-dimensional nonwoven fabric of the present invention. The difference between the fluid penetration rate for the conventional nonwoven fabric and the three-dimensional fabric of the present invention is the Absorbency Rate Increase.

FIG. 1
  absorbent article 1
  absorbent element 2
  barrier film layer 4
  densified embossed channels 5, 6, 7, 8
  longitudinal sides 26
  transverse ends 28
  body-facing cover layer 10
  raised region 50
  semi-raised region 60
  compressed region 70

FIG. 2
  absorbent element 2
  cellulosic fibers 12
  superabsorbent polymer particles 14
  embossed channels 5, 6, 7, 8
  bottom 24
  barrier layer 4
  edges of the absorbent element 16
  peripheral cover extensions 18
  barrier extensions 20
  flange seal 22
  raised region 50
  semi-raised region 60
  compressed region 70

We claim:

1. An absorbent article comprising a body-facing cover layer, a garment facing barrier layer and an absorbent element between the cover layer and the barrier layer, wherein said body-facing cover layer is a non-woven fabric formed from an interconnected network thermoplastic polymer fibers having a bonding pattern made up of a series of discrete dots in a plurality of linear arrays including a first linear array and an adjacent second linear array wherein the dots within the first linear array are closer to adjacent dots within the first linear array than they are to dots in the adjacent second linear array, at least a portion of the non-woven fabric having a three-dimensional thickness profile including a plurality of raised regions, semi-raised regions and compressed regions, the raised regions having a lower fiber density relative to the semi-raised regions, the semi-raised regions having a lower fiber density relative to the compressed regions, wherein said non-woven fabric is formed from a homogeneous blend of high denier fibers and low denier fibers having a denier in a range of from 1.5 denier to 15 denier, wherein the high denier fibers and the low denier fibers differ by at least one denier and wherein the high denier fibers are present in the blend in an amount of from 10 to 90% and the low denier fibers are present in the blend in an amount of from 90 to 10%.

2. The absorbent article according to claim 1 wherein the high denier fibers have a denier in a range of from 4 to 15 and the low denier fibers have a denier in a range of from 2 to 4.

3. The absorbent article according to claim 1 wherein the high denier fiber has a denier of 5 and the low denier fiber has a denier of 3.

4. The absorbent article according to claim 1 wherein the fibers are polypropylene.

5. The absorbent article according to claim 1 wherein the three-dimensional profile is located in a center region of the absorbent article.

6. The absorbent article according to claim 1 wherein the three-dimensional profile is located in a transverse end region of the absorbent article.

7. The absorbent article according to claim 1 wherein the three-dimensional profile is located in a center region and opposite transverse end regions of the absorbent article.

8. The absorbent article according to claim 1 wherein the non-woven fabric is a carded web.

9. The absorbent article according to claim 1 wherein a surface active agent is present on said fabric.

10. The absorbent article according to claim 1 wherein the compressed regions of the non-woven fabric have a fiber density in a range of about 0.05 g/cc to about 0.17 g/cc and a thickness of from about 0.005 mm to about 0.06 mm; the semi-raised regions of the non-woven fabric have a fiber density of from about 0.04 g/cc to about 0.11 g/cc and a thickness from about 1.5 to 40 times the thickness of the compressed regions; and the raised regions of the non-woven fabric have fiber density in a range of from 0.027 g/cc to about 0.07 g/cc and a thickness from about 6 to 800 times the thickness of the compressed regions.

11. The absorbent article according to claim 1 wherein the raised regions have a pyramidal shape.

12. The absorbent article according to claim 1 wherein the nonwoven fabric is thermally bonded having a bond area that comprises from 10 to 40 percent of the total nonwoven fabric area.

13. The absorbent article according to claim 1 wherein the nonwoven fabric is a thermobonded carded web having a titanium dioxide content between about 1 to 6 weight percent.

14. The absorbent article according to claim 13 wherein the nonwoven fabric is treated with a durable hydrophilic surface active agent.

15. The absorbent article according to claim 1 wherein the compressed area is a series of discontinuous bond areas in a pattern of an intermittent series of discrete dots in a linear array.

16. The absorbent article according to claim 15 wherein the discrete dots are spaced apart by a distance from about 0.05 mm to about 5 mm.

17. The absorbent article according to claim 1 wherein the article has a pair of opposite longitudinal sides and opposite transverse ends and further comprising a first pair of embossed channels, each channel located in a central region of the article adjacent to and inward from a respective longitudinal side, and a second pair of embossed channels, each of said second channels being located adjacent to and inward from a respective transverse end of the article.

18. The absorbent article according to claim 1 wherein the absorbent article is selected from the group consisting of disposable diapers, sanitary napkins, panty liners and incontinence devices.

* * * * *